United States Patent
Sasai et al.

(10) Patent No.: US 10,487,310 B2
(45) Date of Patent: Nov. 26, 2019

(54) VESSEL FOR CULTURING HUMAN ES CELLS

(71) Applicants: RIKEN, Wako-shi (JP); SUMITOMO BAKELITE CO., LTD., Shinagawa-ku (JP)

(72) Inventors: Yoshiki Sasai; Keiko Muguruma, Muko (JP); Ryouhei Tsukada, Kobe (JP); Hayao Tanaka, Akita (JP)

(73) Assignees: RIKEN, Wako-shi (JP); SUMITOMO BAKELITE CO., LTD., Shinagawa-ku (JP)

( * ) Notice: Subject to any disclaimer, the term of this patent is extended or adjusted under 35 U.S.C. 154(b) by 0 days.

(21) Appl. No.: 14/406,370

(22) PCT Filed: Jun. 7, 2013

(86) PCT No.: PCT/JP2013/065891
§ 371 (c)(1),
(2) Date: Dec. 8, 2014

(87) PCT Pub. No.: WO2013/183777
PCT Pub. Date: Dec. 12, 2013

(65) Prior Publication Data
US 2015/0140652 A1    May 21, 2015

(30) Foreign Application Priority Data
Jun. 8, 2012  (JP) .................... 2012-131430

(51) Int. Cl.
  *C12N 5/0735*  (2010.01)
  *C12M 1/32*    (2006.01)
(Continued)

(52) U.S. Cl.
  CPC .......... *C12N 5/0606* (2013.01); *C12M 21/06* (2013.01); *C12M 23/12* (2013.01); *C12M 23/20* (2013.01); *C12M 25/06* (2013.01)

(58) Field of Classification Search
  CPC ....... C12N 5/606; C12M 21/06; C12M 23/06; C12M 23/12; C12M 23/20
(Continued)

(56) References Cited

U.S. PATENT DOCUMENTS

2004/0180428 A1* 9/2004 Takeshita ............... C12M 35/00
                                                             435/325
2010/0221768 A1   9/2010 Akai et al.
(Continued)

FOREIGN PATENT DOCUMENTS

EP  2 088 190 A1   8/2009
EP  2 522 716 A1   11/2012
(Continued)

OTHER PUBLICATIONS

Machine Translation of JP06327462A (Year: 2018).*
(Continued)

*Primary Examiner* — Michael L Hobbs
(74) *Attorney, Agent, or Firm* — Oblon, McClelland, Maier & Neustadt, L.L.P.

(57) ABSTRACT

Provided are a culture vessel with which an embryonic body can be formed efficiently from human embryonic stem cells, and a method for culturing human embryonic stem cells using the vessel. There is provided a vessel for culturing human embryonic stem cells, the culture vessel having two or more wells (1), wherein each of the wells (1) has a tubular body (2) and a funnel-shaped bottom (3) provided at one end of the body (2), the bottom (3) being a concave curved surface at the center (4) of the bottom (3) and the bottom (3) having an opening angle (θ) in range of 60 to 100°. There is (Continued)

provided a method for culturing human embryonic stem cells by using said vessel for culturing human embryonic stem cells.

20 Claims, 2 Drawing Sheets

(51) Int. Cl.
*C12M 3/00* (2006.01)
*C12M 1/00* (2006.01)
*C12M 1/12* (2006.01)

(58) Field of Classification Search
USPC ..................................................... 435/305.2
See application file for complete search history.

(56) References Cited

U.S. PATENT DOCUMENTS

| | | |
|---|---|---|
| 2013/0122580 A1 | 5/2013 | Tsukada et al. |
| 2014/0011269 A1 | 1/2014 | Sakura et al. |
| 2014/0322806 A1* | 10/2014 | Bennett ................. C12M 23/02 435/325 |

FOREIGN PATENT DOCUMENTS

| | | | | |
|---|---|---|---|---|
| JP | 06327462 A | * | 11/1994 | ............ C12M 23/54 |
| JP | 2004 254622 | | 9/2004 | |
| JP | 2008 99662 | | 5/2008 | |
| JP | 2008 178367 | | 8/2008 | |
| JP | 2010 94045 | | 4/2010 | |
| JP | 2011 131 | | 1/2011 | |
| JP | 2012 210166 | | 11/2012 | |
| WO | 2011 083768 | | 7/2011 | |
| WO | WO 2012/133514 A1 | | 10/2012 | |

OTHER PUBLICATIONS

Suemori, H., et al., "Efficient establishment of human embryonic stem cell lines and long-term maintenance with stable karyotype by enzymatic bulk passage", Biochemical and Biophysical Research Communications, vol. 345, pp. 926-932, (2006).

International Search Report dated Sep. 10, 2013 in PCT/JP13/065891 Filed Jun. 7, 2013.

Extended European Search Report dated Jan. 4, 2016 in Patent Application No. 13801374.3.

"The physiological control of mammalian vocalization"—J.D. Newman (Ed.) (Plenum Press. New York., 1988), Electroencephalography and Clinical Neurophysiology, Elsevier, vol. 76, No. 1, XP024295175, Jul. 31, 1990, pp. 92.

* cited by examiner

VESSEL FOR CULTURING HUMAN ES CELLS

TECHNICAL FIELD

The present disclosure relates to a culture vessel for culturing human embryonic stem cells and a culture method using the vessel.

BACKGROUND ART

Embryonic stem cells (ES cells) have pluripotency to differentiate into various tissue cells. Various researches have been made to utilize this potency for application to the field of so-called regeneration medical care, namely, repairing cells lost due to diseases, accidents or the like and recovering the tissues (see Patent document 1 for example).

ES cells have diversity to allow differentiation into various cells. It involves correlation among cells, and one example thereof is formation of a cell mass called an embryonic body (EB). This cell mass is formed by suspension culture of ES cells, iPS cells or the like. After culturing for about 2 weeks in a state where the cell mass is formed, differentiation into various cell types can be observed. Therefore, the embryonic body is used as a general method to examine pluripotency of cells.

A method used most widely for culturing ES cells in a suspended state is a hanging drop culture. The hanging drop culture is a method of culturing cells in a culture solution hanging like a water drop. However, this method causes some problems, for example, the success rate in embryonic body formation is low, microscopic observation is impossible, and the operations are arduous. For solving these problems, for example, a culture vessel provided with a water-insoluble cured coating film formed on the inner surface of the vessel by curing a water-soluble resin coating film is proposed (see Patent document 2 for example).

The above-mentioned Patent document 1 (JP 2008-99662) and Patent document 2 (JP 2008-178367) are incorporated herein by reference.

PRIOR ART DOCUMENTS

Patent Documents

Patent document 1: JP 2008-99662
Patent document 2: JP 2008-178367

DISCLOSURE OF INVENTION

Problem to be Solved by the Invention

At present, mouse ES cells are used usually in researches of ES cells. From the viewpoint of clinical application, researches and developments using human ES cells are required. However, human ES cells cause cell death more easily in comparison with mouse ES cells, resulting in a problem of difficulty in obtaining an embryonic body. Therefor, there has been demand for a culture vessel with which an embryonic body can be formed from human ES cells more efficiently.

In one or a plurality of embodiments, the present disclosure provides a culture vessel with which an embryonic body can be formed efficiently from human ES cells.

Means for Solving Problem

In one or a plurality of embodiments, the present disclosure relates to a vessel for culturing human ES cells. The culture vessel for human ES cells has two or more wells. Each of the wells has a tubular body and a funnel-shaped bottom provided at one end of the body, the bottom has a concave curved surface at the center of the bottom, and the opening angle of the bottom is in a range of 60 to 1000.

Effects of the Invention

With the culture vessel according to the present disclosure, it is possible to culture an embryonic body form human ES cells efficiently.

DESCRIPTION OF THE INVENTION

Figure 1:
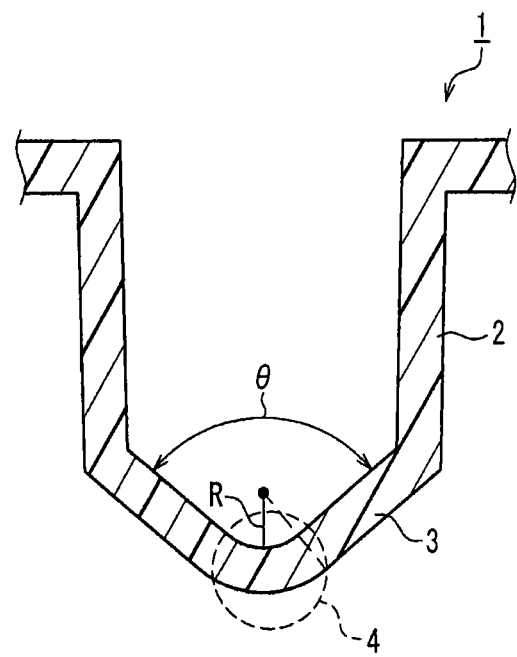
FIG. 1 is a cross-sectional view of a well in a culture vessel according to Embodiment 1.

The culture vessel according to the present disclosure is based on a finding that an embryonic body can be formed efficiently from human ES cells by shaping the well bottom like a funnel having an opening angle in a range of 60 to 100° and forming the center to be round-shaped concavity.

Though it has not been clarified why the culture vessel according to the present disclosure is suitable for culturing human ES cells and thus an embryonic body can be formed efficiently from human ES cells by use of the culture vessel according to the present disclosure, the reason can be deduced as follows. Since the well bottom has an inclined surface with an opening angle in a range of 60 to 100°, when cells dispersed into single cells are dispensed into the wells, the area where the cells are gathered is decreased in an observation from above. As a result, the cell density at the ends where the cells are gathered becomes increased, thereby a single cell aggregate will be formed easily. Further, since the center of each well has a concave curved surface, the cells in the vicinity of the lowest bottom of the well can be incorporated easily into the aggregate, and thus a single cell aggregate will be formed easily. However, the present disclosure is not limited to these mechanisms.

That is, the present disclosure may relate to the following one or a plurality of embodiments.

[1] A culture vessel for culturing human embryonic stem cells (human ES cells), wherein:
the culture vessel has two or more wells,
each of the wells has a tubular body and a funnel-shaped bottom provided at one end of the body,
the bottom has a concave curved surface at the center of the bottom, and
the bottom has an opening angle in a range of 60 to 1000.

[2] The culture vessel according to [1], wherein the radius of curvature of the inner surface of the center of the bottom is in a range of 0.5 to 1.5 mm.

[3] The culture vessel according to [1] or [2], wherein a coating layer formed by use of a water-soluble resin expressed by Formula (Ia) or (Ib) below is applied on at least the inner surface of the bottom of the well:

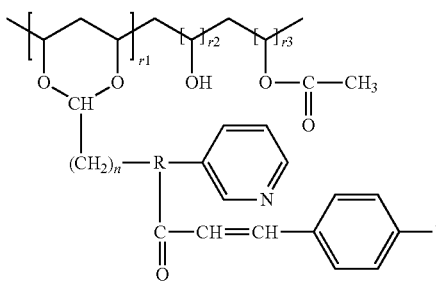

(Ia)

in Formula (Ia), R is an alkyl group having carbonyl and amine, r1 is in range of 1 to 1000, r2 is in a range of 40 to 4995, r3 is in a range of 0 to 4000, and n is 1, 2 or 3;

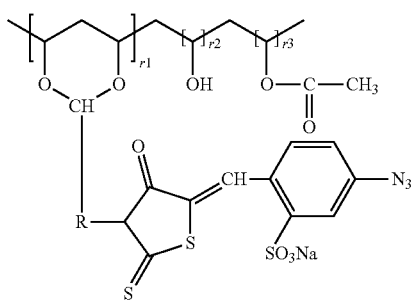

(Ib)

in Formula (Ib), R is an alkyl group having carbonyl and amine, r1 is in range of 1 to 1000, r2 is in a range of 40 to 4995, and r3 is in a range of 0 to 4000.

[4] The culture vessel according to any one of [1] to [3], wherein each of the wells has a side wall surface whose side wall inner surfaces are substantially parallel, an inclined surface formed at one end of the side wall surface and whose side wall inner surface decreases its diameter toward the bottom surface, and a partially spherical center formed at one end of the inclined surface.

[5] The culture vessel according to any one of [1] to [4], wherein the body is substantially cylindrical.

[6] The culture vessel according to any one of [1] to [5], wherein, in each of the wells, the cross section taken along the center line of the body has a shape as follows: the body is rectangular, the bottom is substantially V-shaped, and the center of the bottom is arc-shaped.

[7] The culture vessel according to any one of [1] to [6], which is a 96-well plate.

[8] A method for culturing human embryonic stem cells by using a culture vessel, wherein:
the culture vessel has two or more wells,
each of the wells has a tubular body and a funnel-shaped bottom provided at one end of the body,
the bottom has a concave curved surface at the center of the bottom, and
the bottom has an opening angle in a range of 60 to 100°.

[9] The method according to [8], wherein the radius of curvature of the inner surface of the center of the bottom is in a range of 0.5 to 1.5 mm.

[10] A method for culturing human ES cells by using the culture vessel according to any one of [1] to [7].

[Culture Vessel]

In one or a plurality of embodiments, the present disclosure relates to a vessel for culturing human ES cells. The culture vessel for human ES cells has two or more wells. With the culture vessel according to the present disclosure, an embryonic body can be formed efficiently from human ES cells. Further, as the culture vessel according to the present disclosure enables to form an embryonic body efficiently, it is suitable for culturing ES cells, particularly human ES cells. It is suitable for culturing human ES cells in comparison with mouse ES cells, for example.

Each of the wells has a tubular body and a funnel-shaped bottom provided at one end of the body, and the center of the bottom has a curved surface. That is, the bottom can be expressed as a reversed cone whose vertex is partially spherical. The body may be substantially cylindrical, for example. In one or a plurality of embodiments of the well, the cross section taken along the center line of the well may be rectangular for the body, and substantial V-shaped for the bottom with an arc-shaped center. In one or a plurality of embodiments of the well, the joint of the body and the bottom is preferably a curved surface.

Further, in one or a plurality of embodiments, the well may be shaped to have a side wall surface with a substantially parallel side wall inner surfaces, an inclined surface formed at one end of the side wall surface with the side wall inner surface decreasing its diameter toward the bottom surface, and a partially spherical center formed at one end of the inclined surface.

The opening angle of the bottom is in a range of 60 to 100°. From the viewpoint of decreasing the area where the cells are gathered in an observation from above at the time of inoculation of the cells, preferably it is more than 60° and not more than 100°; more preferably 70 to 100°; and further preferably 80 to 90°. The "opening angle" in the present disclosure denotes an angle formed by the opposing parts of the inclined surface at the bottom of the well, and for example, it is the angle indicated as θ in FIG. 1.

The radius of curvature of the inner surface of the center of the bottom is preferably 0.5 to 1.5 mm such that the cells in the vicinity of the lowest bottom of the well will be incorporated easily into the aggregate. From the viewpoint of easy observation of the cell aggregate in the optical microscopy, 0.7 to 1.2 mm is more preferable, and further preferably, 0.9 to 1.1 mm. The "radius of curvature of the inner surface of the center" in the present disclosure denotes the curved surface at the tip end of the well bottom, and for example, it is the radius of curvature indicated with R in FIG. 1. The radius of curvature of the inner surface of the center can be measured with a laser rangefinder or by actually measuring the section of a molded product.

In one or a plurality of embodiments, preferably the inner surface of at least the bottom of the well is subjected to a treatment to reduce adhesion of cells. The "treatment to reduce adhesion of cells" in the present disclosure denotes a treatment to reduce the adhesiveness of the well inner surface with respect to the cells. Reduction of adhesiveness includes for example, difficulty in adhesion between the well inner surface and the cells, and non-adhesion between the well inner surface and the cells.

One example of the treatment to reduce adhesiveness is hydrophilicity treatment of the well inner surface. Examples of the hydrophilicity treatment include formation of a coating layer by use of a water-soluble resin, and formation of coating layer by use of a hydrophilic resin. In the present disclosure, "water-soluble resin" is a resin that is hydrated due to ionic bond or hydrogen bond with water molecules so as to dissolve in water, more specifically a resin that can be dissolved in an amount of 1.0 g or more with respect to 100 g of 25° C. water. The water-soluble resin may be the one having ionic or polar side chain of a necessary and sufficient amount with respect to the main chain within the molecule in order to be dissolved in water.

Examples of the water-soluble resin include saponified polyvinyl acetate, polyvinyl pyrrolidone, polyethylene glycol, polyacrylamide, polymethacrylamide, polyhydroxy ethyl methacrylate, polypentaerythritol triacrylate, polypentaerythritol tetraacrylate, polydiethylene glycol diacrylate, and a copolymer of monomers constituting the same; and a copolymer of 2-methacryloyl oxyethyl phosphorylcholine and any other monomer (e.g., butylmethacrylate). Among them, a structure of at least one of saponified polyvinyl acetate, polyvinyl pyrrolidone and polyethylene glycol and a functional group mentioned below is preferred. Thereby, it is possible to suppress stimulation to various cells and to improve the speed of formation of the cell aggregate mass, formation rate, and the quality of the formed cell aggregate mass.

Examples of the saponified substance of polyvinyl acetate include a copolymer of either polyvinyl alcohol or vinyl alcohol and any other compound; and a saponified substance of denatured vinyl acetate and vinyl alcohol. The denatured vinyl acetate is denatured in advance with a reactive group such as a hydrophilic group, a hydrophobic group, anion, cation, an amide group or an acetoacetyl group. Though there is no particular limitation, the average polymerization degree of the polymer is preferably in a range of 100 to 10,000, and more preferably 200 to 5,000 from the viewpoint of easy formation of a uniform coating film on the inner surface of the culture vessel and further improvement in workability. Though there is no particular limitation, the saponification degree of the saponified substance of polyvinyl acetate is in a range of 20 to 100 mol % in the overall polyvinyl acetate, and more preferably 50 to 95 mol %.

The water-soluble resin is preferably a water-soluble resin having a functional group in its side chain for curing. Examples of the functional group for curing include functional groups of radiation response, photosensitivity, and thermal reactivity. Examples of the photosensitive functional group include a diazo group, an azido group, and a cinnamoyl group. Examples of the thermal reactive functional groups and radiation response functional groups include a vinyl group and an epoxy group. Among them, a water-soluble resin having a photosensitive functional group is preferred since curing treatment can be carried out quickly and curing can be carried out with simple equipment.

For the water-soluble resin, a water-soluble resin having an azido group is preferred since a uniform coating layer can be formed in a wavelength of 300 to 500 nm and the amount of cell adhesion can be reduced to improve the efficiency in formation of a cell aggregate mass. The water-soluble resin expressed by Formula (Ia) or (Ib) is further preferred.

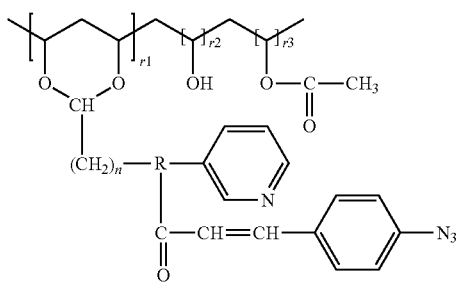

(Ia)

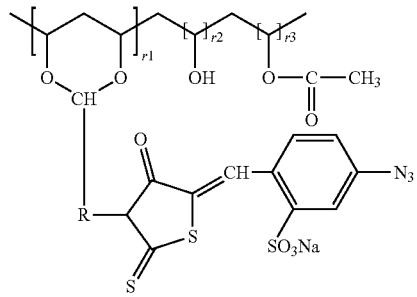

(Ib)

In Formulae (Ia) and (Ib), R denotes an alkyl group having carbonyl and amine, and from the viewpoint of easy synthesis of a polar side chain, the group expressed by Formula (II) below is preferred.

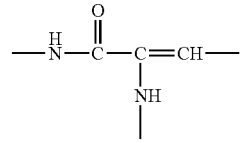

(II)

In Formula (Ia), r1 is 1 to 1000, r2 is 40 to 4995, r3 is 0 to 4000, and n indicates 1, 2, or 3. In Formula (Ib), r1 is 1 to 1000, r2 is 40 to 4995, and r3 is 0 to 4000.

Though there is no particular limitation, examples of the hydrophilic resin include poly-2-hydroxyethyl methacrylate (poly-HEMA), a polymer compound containing a phosphorylcholine group, and a polymer compound containing a polyethylene glycol chain.

Though there is no particular limitation, examples of the thickness of the coating layer is preferably in a range of 100 to 5,000 nm, and more preferably 150 to 1,000 nm from the viewpoint of reducing the physical stimulation applied from a culture substrate (well) to the cells and reducing the amount of protein captured into the coating layer so as to suppress adhesion of the cells to the well via the protein and further improve the success rate of cell aggregate mass formation.

Though there is no particular limitation on the materials of the culture vessel according to present disclosure, a resin is preferred since the culture vessel can be made disposable and can be molded easily. Examples of the resin include polyolefin-based resins or cyclic polyolefin-based resins such as a polypropylene resin, a polyethylene resin and an ethylene-propylene copolymer; polystyrene-based resins such as polystyrene and acrylonitrile-butadiene-styrene-based resin; methacrylic resins such as polycarbonate resin, a polyethylene terephthalate resin and a polymethyl methacrylate resin; fluorine-based resins such as a vinyl chloride resin, a polybutylene terephthalate resin, a polyarylate resin, a polysulphone resin, a polyether sulphone resin, a polyether ether ketone resin, a polyetherimide resin, and polytetrafluoroethylene; acrylic resins such as a polymethylpentene resin, and polyacrylonitrile; and cellulosic resins such as a propionate resin. Among them, from the viewpoint of moldability and sterilization capability required for the culture vessel, a polystyrene resin is preferred.

Examples of the shape of the culture vessel according to the present disclosure include vessels like a multi-well plate, a laboratory dish and a flask. Any other shape may be employed as long as it can be located and used under a circumstance for culturing cells, for example, a sheet-like molded product may be used. Among them, from the viewpoint of capable of improving the precision in evaluation and research by use of an aggregate mass, a multi-well plate or a laboratory dish used for producing bioreactor or estimation of medicine efficacy or toxic, research and development of artificial organs etc. are preferred. Though the number of the wells in a multi-well plate is not limited in particular, it is 6, 12, 24, 48, 96 or 384 for example.

A culture vessel according to the present disclosure can be manufactured in the following manner.

First, the above-mentioned resin material is molded by ejection, blowing, injection-blowing or the like to have a desired shape.

In a case where the culture vessel is applied to measurement of a labeled material by use of light-emission or fluorescence phenomenon, it is preferable that the wells are shielded such that the emission or fluorescence does not leak to the adjacent wells. It is realized by molding with a colored resin, by molding a transparent resin and coating the vessel with opaque paint or the like, or by making the vessel opaque by formation of a metallic coating through plating or deposition. Molding of a colored resin is preferred since the operations are simple and easy. It is also possible to add a pigment to a transparent resin and further knead and mold, or a material prepared by kneading a transparent resin and a pigment can be molded. From the viewpoint of dispersion of pigment, it is preferable to mold by using a resin material prepared by kneading a transparent resin and a pigment. The pigment can be selected appropriately according to the desired color without any particular limitations, and the examples include a white pigment and a black pigment. A white pigment is preferred since a further favorable measurement sensibility is obtained and the state of the cell aggregate mass or the existence of a culture solution can be checked easily. An example of the white pigment is titanium oxide. An example of the black pigment is carbon black. From the viewpoint of obtaining a resin molded product that exhibits sufficient light-shielding property and sufficient strength, the amount of the pigment is preferably 7 to 15 wt % for titanium oxide, and 3 to 10 wt % for carbon black. For the light-shielding level, it is preferred that the light transmittance to an adjacent well is smaller. For example, it is 1% or less, preferably 0.1% or less, and more preferably 0.01% or less.

Next, the molded vessel is treated to reduce cell adhesion.

In a case of forming a coating layer using a water-soluble resin, first, the above-mentioned water-soluble resin is made contact with the inner surface of the well. For the contact, for example, spin coating, dipping, or dispensation of a solution of the water-soluble resin into well surfaces is carried out. It is preferable that the water-soluble resin is made contact in a state being dissolved in a solvent. Examples of the solvent include water, and a mixture of water and an organic solvent. Though the concentration of the water-soluble resin to be contacted is not limited in particular, preferably for example, it is in a range of 0.01 to 30 wt %, and more preferably 0.1 to 10 wt % from the viewpoint of obtaining a uniform coating layer, obtaining a sufficient effect in reduction of cell adhesion, and forming a favorable cell aggregate mass.

The water-soluble resin is dried and then cured. Thereby, a resin coating layer having an ionic or polar side chain with a high density is formed. The ionic or polar side chain constituted on the surface is hydrated with water molecules due to either an electrostatic interaction or a hydrogen bond at the time of contact with the culture solution, and the culture vessel surface substantially becomes a dense hydrated layer of water molecules. This hydrated layer suppresses stimulation to the cells from the culture substrate surface, so that a cell aggregate mass with a favorable quality is formed quickly. In this manner, it is possible to prevent the coating layer of the water-soluble resin from being dissolved and freed at the time of the contact of the culture solution, and thus waterproof necessary for a culture vessel can be attained.

On the other hand, in a case of forming a coating layer by using a hydrophilic resin, for example, a 2% ethanol solution of poly-HEMA is dispensed to be 100 μL into each well and the ethanol is evaporated so as to form a layer of poly-HEMA. After the evaporation, washing is conducted by using ultrapure water or a buffer solution, thereby removing excessive poly-HEMA molecules that are not adsorbed onto the vessel surface.

And after the treatment for reducing cell adhesion as mentioned above, sterilization is carried out. Examples of the sterilization include ethylene oxide gas sterilization, hot air sterilization, steam sterilization, radiation sterilization and the like. Radiation sterilization using γ-rays or electron beams is preferred. When large scale production is taken into consideration, γ-ray sterilization is more preferable from the viewpoint of radiation permeability.

[Culture Method]

In one or a plurality of embodiments, the present disclosure relates to a method for culturing human ES cells by using a culture vessel. A culture vessel used in a culture method according to the present disclosure has two or more wells. Each well has a tubular body and a funnel-shaped bottom provided at one end of the body. The center of the bottom has a concave curved surface, and the opening angle of the bottom is in a range of 60 to 100°. Further, in one or a plurality of embodiments, the present disclosure relates to a method for culturing human embryonic stem cells using the culture vessel according to the present disclosure. In the culture method according to the present disclosure, an embryonic body can be formed efficiently from human ES cells by using the above-mentioned culture vessel.

Regarding the culture vessel according to the present disclosure, it is preferable that the radius of curvature of the inner surface of the center of the bottom is in a range of 0.5 to 1.5 mm.

Hereinafter, the culture vessel according to the present disclosure will be explained in detail with reference to favorable embodiments, although the present disclosure is not limited to the following embodiments.

Embodiment 1

Figure 2:
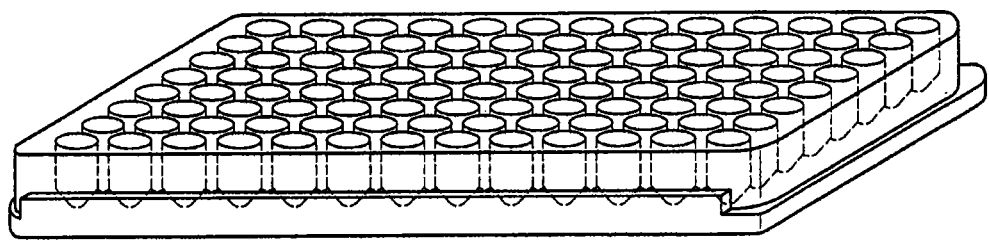
FIG. 2 is a perspective view of a culture vessel according to Embodiment 1.

FIG. 1 is a cross-sectional view of a well of a culture vessel according to Embodiment 1. FIG. 2 is a perspective view of a culture vessel (96-well multi-well plate) according to Embodiment 1. As shown in FIG. 1, the well 1 of the culture vessel according to Embodiment 1 has a substantially tubular body 2 and a funnel-shaped bottom 3, and the bottom 3 has a semi-spherical center 4. The bottom 3 has an inclined surface with an opening angle (θ) of 85°, and the radius of curvature of the inner surface of the center of the bottom is 1.0 mm. The opening angle (θ) can be measured from an angle formed by the opposing inclined surfaces of the bottom 3 as shown in FIG. 1.

The diameter of the opening of the well is preferably 4.0 mm or more for example from the viewpoint of excellent operability in a case of using a multi-dispenser. It is preferably 11.0 mm or less from the viewpoint of increasing the number of wells for one culture vessel.

Although the capacity of one well is not limited in particular, preferably it is in a range of 80 to 500 μL for example since a nutrient medium of a sufficient amount for forming an embryonic body can be added, and in a range of 80 to 200 μL from the viewpoint of reducing the use amount of the medium or a reagent.

Hereinafter, the present disclosure is explained based on the following Example and Comparative Examples, although the present disclosure is not limited thereto.

EXAMPLES

Example 1

Preparation of Culture Vessel

A polystyrene resin (trade name: HF77, manufactured by PS Japan Corporation) was used to mold a 96-well multi-well plate (transverse: 127.6 mm; longitudinal: 85.8 mm; height: 14.0 mm) by ejection. Each well has the shape as shown in FIG. 1. The opening angle at the bottom (θ in FIG. 1) was 85°, and the radius of curvature of the inner surface at the bottom center was 1.0 mm.

The thus obtained plate was subjected to a plasma treatment by using a plasma treatment apparatus (SERIES7000 manufactured by BRANSON/IPC), thereby applying wettability to the plate surface.

(Surface Treatment Using Water-Soluble Resin)

For treating the surface of the well, a water-soluble resin was dissolved in a 25 vol % of aqueous solution of ethanol in a polypropylene vessel provided with a light-shielding property by a colored resin, thereby preparing a 0.3 wt % of water-soluble resin solution. The water-soluble resin used here was polyvinyl alcohol having an azide group at the side chain (manufactured by Toyo Gosei Co., Ltd., AWP (Azide-unit pendant Water soluble Photopolymer; r1=1-1000; r2=4-4995; r3=0-4000; n=1, 2, or 3; R is an alkyl group having carbonyl and amine): a compound expressed by the following Formula (Ia) (average polymerization degree of water-soluble resin: 1600; introduction rate of photosensitive group: 0.65 mol %)).

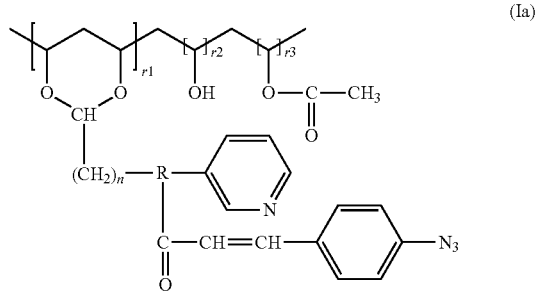

(Ia)

The prepared water-soluble resin solution of 200 μL for one well was introduced into the plasma-treated plate by using an auto-dispenser (Auto Sera Washer-AMW-96SX manufactured by BioTec Co., Ltd.). After dipping for 1 minute, the plate was turned upside down to discard sufficiently the solution. Next, after a primary drying at 25° C. for 17 hours, UV rays of 250 nm was radiated by a UV lamp at 1.0 mW/cm²×30 seconds so as to cure the water-soluble resin. This was washed repeatedly 3 times with ultrapure water, dried, and then irradiated with γ rays at an absorbed dose of 5.8 kGy (an apparatus manufactured by Radia Industry Co., Ltd.) so as to obtain a culture vessel (plate).

[Formation of Cell Aggregate Mass by SFEBq Method Using Human ES Cells Dispersed into Single Cells]

In accordance with a process as stated in Suemori et al., Biochem Biophys Res Commun. 345, 926-32 (2006), undifferentiated human embryonic stem cells were cultured at 37° C., under 2% $CO_2$ on a plastic culture dish where mouse embryonic fibroblast (MEF, inactivated by mitomycin treatment) had been inoculated as a cell feeder layer. It should be noted that Suemori et al., Biochem Biophys Res Commun. 345, 926-32 (2006) is incorporated herein by reference. The culture solution used here was prepared by adding KSR (Invitrogen/Gibco-BRL) at a final concentration of 20%, 1×NEAA (non-essential amino acids; Invitrogen/Gibco BRL), 2 mM L-glutamic acid, 0.1 mM 2-mercaptoethanol and 5 ng/ml bFGF (Upstate) to D-MEM/F12 (Sigma D6421). Subculture was carried out every third or fourth days. By using a dissociation solution (prepared by adding 0.25% trypsin, 1 mg/ml collagenase IV solution, 1 mM $CaCl_2$ and KSR at a final concentration of 20% to phosphate buffered saline; all of which are manufactured by Invitrogen/Gibco-BRL), human ES cells were dissociated from the feeder layer, and dispersed into small cell masses (numerically about 10 to 20) by pipetting, and then they were inoculated on a feeder layer which had been formed by inoculating MEF on the previous day. The human embryonic stem cells used here were embryonic stem cells (KhES-1, KhES-2 and KhES-3) derived from a human blastocyst established by the laboratory of Norio NAKATSUJI at Institute for Frontier Medical Sciences, Kyoto University. The cells were allocated in accordance with the governmental guideline regarding human embryonic stem cells (mainly KhES-1).

The effect of the well shape on the re-aggregation of the human embryonic stem cells after dispersion into single cells was reviewed in the following manner. One hour before the isolation of the cells from the feeder layer, ROCK inhibitor Y-27632 at a concentration of 10 μM was added to the human ES cells cultured as mentioned above, and then the human ES cells were dissociated as small cell masses from the feeder layer. Further, for removing contaminating feeder cells, the dissociated small cell masses were placed on a cell-adhesive culture plate (0.1% gelatin coat) and cultured in a maintenance culture medium at 37° C. for 1 hour, thereby adsorbing the contaminating feeder cells onto the culture plate. The human ES cell masses from which the feeder cells had been removed were dispersed into single cells by TrypLE Express including 0.05 mg/ml DNaseI (Roche) and 10 μM of ROCK inhibitor Y-27632, and they were placed in a surface-treated culture vessel in a state suspended in a 100 μl differentiation medium so as to make 9×10³ cells per well thereby forming quickly aggregate masses, followed by an incubation at 37° C. in 5% $CO_2$ for 6 days, and the state of the re-aggregated cell mass was evaluated. The differentiation medium used here was prepared by adding KSR at a final concentration of 20%, 20 μM Y-27632, 1×NEAA, 1 mM pyruvic acid, 0.1 mM 2-mercaptoethanol, 100 U/ml penicillin and 100 μg/ml streptomycin to G-MEM (Invitrogen).

Figure 3:
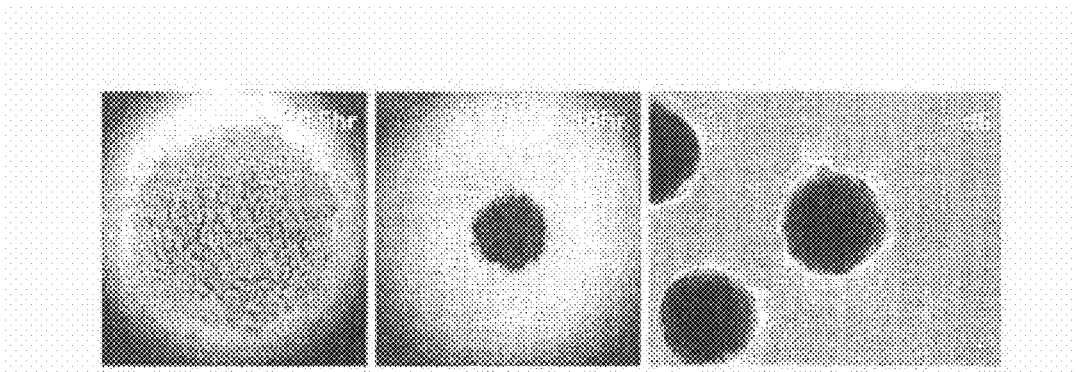
FIG. 3 includes microphotographs of cell aggregate masses during a human ES cell culture in Example 1.

The evaluation was carried out in accordance with the criteria A-C below. The results are shown in Table 1 below. The evaluation was carried out with n=5 to 10. FIG. 3 includes photographs taken in a microscopic observation of cell aggregate masses formed by culturing human ES cells.

The microscopic photographs in FIG. 3 show the shapes of the cell masses after 0.5 hours, 18 hours and 6 days culture from the left in this order.
A: a single aggregate mass is formed in a well
B: an aggregate mass is formed but a plurality of small aggregate masses are formed to surround the mass.
C: no aggregate mass is formed.

Comparative Example 1

Figure 4:
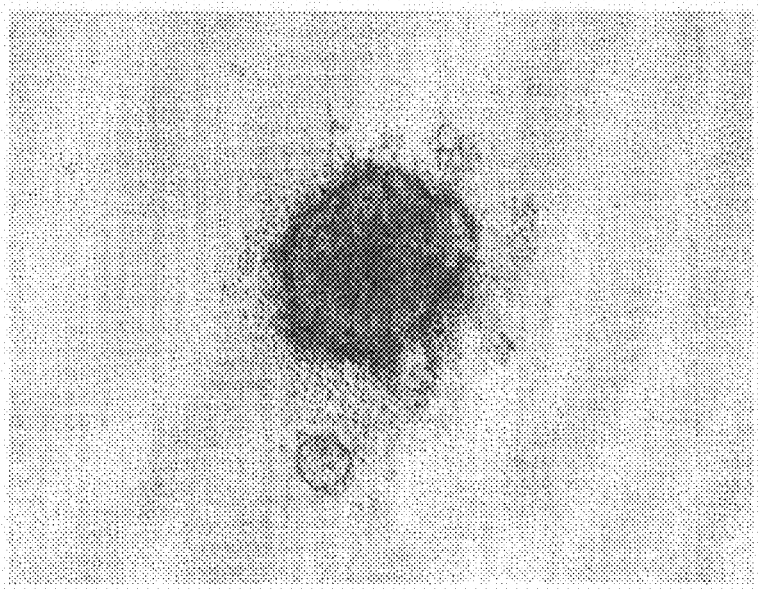
FIG. 4 is a microphotograph of cell aggregate masses during a human ES cell culture in Comparative Example 1.

A multi-well plate was obtained and used for forming and evaluating cell aggregate mass in the same manner as in Example 1, except that a commercially available multi-well plate of a U-shaped bottom was employed. The results are shown in Table 1 below. The commercially available multi-well plate was MS-309UR manufactured by Sumitomo Bakelite Co., Ltd. (transverse: 127.6 mm; longitudinal: 85.8 mm; height: 14.0 mm; diameter of opening of well: 7.0 mm; depth of well: 10.0 mm; radius of curvature of bottom inner surface: 3.2 mm). The evaluation was carried out with n=5 to 10. FIG. 4 shows a photograph taken in a microscopic observation of the formed cell aggregate mass (culture period: 2 days)

Comparative Example 2

A multi-well plate was obtained and used for forming and evaluating cell aggregate masses in the same manner as in Example 1, except that a commercially available multi-well plate (MS-9096M manufactured by Sumitomo Bakelite Co., Ltd.; U-shaped bottom; opening angle: 19°; radius of curvature of bottom surface: 2.0 mm) was employed. The results are shown in Table 1 below.

TABLE 1

| | Example 1 | Comparative Example 1 | Comparative Example 2 |
|---|---|---|---|
| A: a single aggregate mass is formed in a well | 100% | 27-58% | 48-82% |
| B: an aggregate mass is formed but a plurality of small aggregate masses are formed to surround the mass | — | 42-73% | 18-52% |
| C: No aggregate mass is formed | — | — | — |

As shown in Table 1, in the culture vessel of Example 1, formation of a single aggregate mass was recognized for all of the wells. On the other hand, for the plates of Comparative Examples 1 and 2, the efficiency in formation of aggregate mass was degraded considerably, and a plurality of aggregate masses were formed respectively in the wells of 42 to 73% and 18 to 52%.

As shown in FIG. 3, in Example 1, a single aggregate mass was recognized from 18 hours after the start of the culture, and finally, a single aggregate mass was formed in the well. On the other hand, in Comparative Example 1 as show in FIG. 4, a plurality of small aggregate masses were recognized around a large aggregate mass. Although no drawing for Comparative Example 2 is presented, small aggregate masses similar to those in FIG. 4 were recognized.

INDUSTRIAL APPLICABILITY

The present disclosure is useful in the research of human ES cells and the medical field or the like, such as regeneration medical care.

The embodiments have been described, hereinabove. It will be apparent to those skilled in the art that the above methods and apparatuses may incorporate changes and modifications without departing from the general scope of the present disclosure. It is intended to include all such modifications and alterations insofar as they come within the scope of the appended claims or the equivalents thereof. Although the description above contains much specificity, this should not be construed as limiting the scope of the disclosure, but as merely providing illustrations of some of the embodiments of the present disclosure. Various other embodiments and ramifications are possible within its scope.

The invention claimed is:

1. A culture vessel for culturing human embryonic stem cells, comprising:
   a plurality of wells each comprising a tubular body, a bottom portion having a funnel shape and formed at one end of the tubular body, and a concave curved portion formed at a center portion of the bottom portion,
   wherein the funnel shape of the bottom portion has an opening angle in a range of from 70° to 100°, and the concave curved portion has a radius of curvature in a range of from 0.5 mm to 1.5 mm.

2. The culture vessel according to claim 1, further comprising:
   a coating layer formed on an inner surface of the bottom portion, and formed from a water-soluble resin of Formula (Ia) or (Ib)

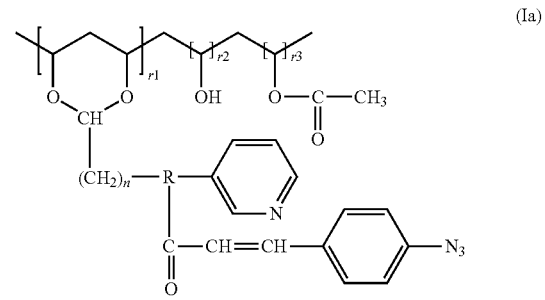

(Ia)

in Formula (Ia), R is an alkyl group having carbonyl and amine, r1 is in a range of from 1 to 1000, r2 is in a range of from 40 to 4995, r3 is in a range of from 0 to 4000, and n is 1, 2 or 3,

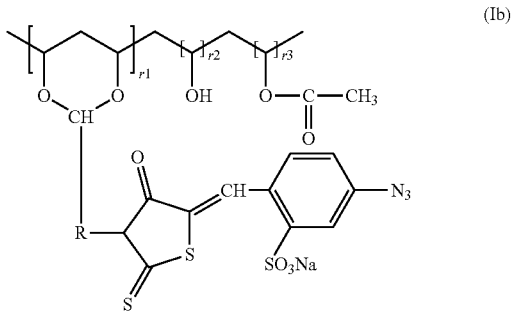

(Ib)

in Formula (Ib), R is an alkyl group having carbonyl and amine, r1 is in a range of from 1 to 1000, r2 is in a range of from 40 to 4995, and r3 is in a range of from 0 to 4000.

3. The culture vessel according to claim 1, wherein each of the wells has a side wall, an inclined wall formed at one end of the side wall, and a partially spherical center formed at one end of the inclined wall, the side wall has an inner surface which is substantially parallel, and the inclined wall has an inner surface having a diameter that decreases toward the center portion of the bottom portion.

4. The culture vessel according to claim 1, wherein the tubular body is substantially cylindrical.

5. The culture vessel according to claim 1, wherein each of the wells has a cross section taken along a center line of the tubular body, and a shape of the cross section has a rectangular portion corresponding to the tubular body, a substantially V-shaped portion corresponding to the bottom portion, and an arc-shaped portion corresponding to the concave curved portion.

6. The culture vessel according to claim 1, wherein the culture vessel comprises 96 wells and forms a 96-well plate.

7. A method for culturing human embryonic stem cells, comprising:
incubating human embryonic stem cells in a well,
wherein the well comprises a tubular body, a bottom portion having a funnel shape and formed at one end of the tubular body, and a concave curved portion formed at a center portion of the bottom portion, the funnel shape of the bottom portion has an opening angle in a range of from 70° to 100°, and the concave curved portion has a radius of curvature in a range of from 0.5 mm to 1.5 mm.

8. A method for culturing human embryonic stem cells, comprising:
incubating human embryonic stem cells in the culture vessel according to claim 1.

9. A method for culturing human embryonic stem cells, comprising:
incubating human embryonic stem cells in the culture vessel according to claim 2.

10. A method for culturing human embryonic stem cells, comprising:
incubating human embryonic stem cells in the culture vessel according to claim 3.

11. A method for culturing human embryonic stem cells, comprising:
incubating human embryonic stem cells in the culture vessel according to claim 4.

12. A method for culturing human embryonic stem cells, comprising:
incubating human embryonic stem cells in the culture vessel according to claim 5.

13. The culture vessel according to claim 2, wherein the coating layer has a thickness in a range of from 100 nm to 5,000 nm.

14. The culture vessel according to claim 1, wherein the opening angle is in a range of 80° to 100°.

15. The culture vessel according to claim 3, further comprising:
a coating layer formed on an inner surface of the bottom portion and formed from a water-soluble resin of Formula (Ia) or (Ib)

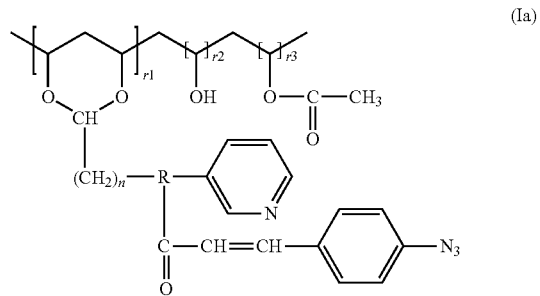

(Ia)

where in Formula (Ia), R is an alkyl group having carbonyl and amine, r1 is in a range of from 1 to 1000, r2 is in a range of from 40 to 4995, r3 is in a range of from 0 to 4000, and n is 1, 2 or 3,

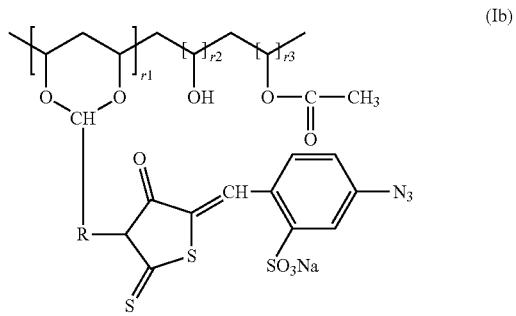

(Ib)

and in Formula (Ib), R is an alkyl group having carbonyl and amine, r1 is in a range of from 1 to 1000, r2 is in a range of from 40 to 4995, and r3 is in a range of from 0 to 4000.

16. The culture vessel according to claim 1, wherein the opening angle is in a range of 75° to 100°.

17. A method for culturing human embryonic stem cells, comprising:
incubating human embryonic stem cells in the culture vessel according to claim 6.

18. The culture vessel according to claim 2, wherein the tubular body is substantially cylindrical.

19. The culture vessel according to claim 2, wherein each of the wells has a cross section taken along a center line of the tubular body, and a shape of the cross section has a rectangular portion corresponding to the tubular body, a substantially V-shaped portion corresponding to the bottom portion, and an arc-shaped portion corresponding to the concave curved portion.

20. The culture vessel according to claim 2, wherein the culture vessel comprises 96 wells and forms a 96-well plate.

* * * * *